US008862438B2

(12) United States Patent
Drabish et al.

(10) Patent No.: US 8,862,438 B2
(45) Date of Patent: Oct. 14, 2014

(54) METHOD FOR IMPROVING THE PREDICTION OF POLYMER PROPERTIES (75) Inventors: Jeffrey B. Drabish, Elkview, WV (US); John R. Parrish, Charleston, WV (US); Marcel Schaefer, Wesseling (DE); Ivan J. Hartley, Victoria, TX (US); Paul K. Samples, Scott Depot, WV (US); Mark L. Nelson, Charleston, WV (US)

(73) Assignee: Dow Global Technologies LLC, Midland, MI (US)

( * ) Notice: Subject to any disclaimer, the term of this patent is extended or adjusted under 35 U.S.C. 154(b) by 245 days.

(21) Appl. No.: 12/670,885

(22) PCT Filed: Jul. 24, 2008

(86) PCT No.: PCT/US2008/071027
§ 371 (c)(1),
(2), (4) Date: Jan. 27, 2010

(87) PCT Pub. No.: WO2009/020772
PCT Pub. Date: Feb. 12, 2009

(65) Prior Publication Data
US 2010/0209307 A1 Aug. 19, 2010

Related U.S. Application Data (60) Provisional application No. 60/954,506, filed on Aug. 7, 2007.

(51) Int. Cl.
G06F 7/60 (2006.01)
G06G 7/48 (2006.01)
B01J 19/00 (2006.01)
G01N 35/08 (2006.01)
G06F 19/00 (2011.01)

(52) U.S. Cl.
CPC .................................... *G06F 19/704* (2013.01)
USPC .................... 703/2; 703/12; 422/131; 436/55

(58) Field of Classification Search
CPC .. G05B 23/024; G05B 23/0272; G05B 13/04; G05B 13/048; G06F 19/704; G06F 19/16; G06F 17/5009; G06F 19/707; G06F 19/18; G06F 19/706; G06F 17/10; G06F 17/5018; G06F 19/12; G06F 19/70; G06F 19/701; G06F 2217/10; G06F 19/20; G06F 19/24; G06F 19/3437; G06F 2217/08; G06F 2217/44; G06F 15/00; G06F 19/26; G06F 19/702; G06F 19/708; G06F 2217/16; C12Q 1/6837; C12Q 2545/101; C12Q 2600/106; G01N 15/0266; G01N 21/274; G01N 35/00712; G01N 35/00871
USPC ............................. 422/131; 703/2, 12; 436/55
See application file for complete search history.

(56) References Cited

U.S. PATENT DOCUMENTS 5,260,882 A 11/1993 Blanco et al.
5,550,630 A 8/1996 Chrastil
(Continued)

OTHER PUBLICATIONS

Ardell, George G., et al., Model Prediction for Reactor Control, Chemical Engineering Progress, 1983, pp. 77-83, Union Carbide Corp., South Charleston, West Virginia.
Mcauley, K. B. et al., Nonlinear Product Property Control in Industrial Gas-Phase Polyethylene Reactors, AIChE Journal, 1993, pp. 855-866, vol. 39, No. 5.

(Continued)

Primary Examiner — Dean Kwak (57) ABSTRACT

A method for improving the prediction of polymer properties and a system having improved polymer property prediction capabilities is provided. The method for improving the prediction of polymer properties comprises: (1) providing a polymer; (2) providing a prediction model; (3) utilizing said prediction model to define an average polymer property prediction value; (4) determining a feasible range; (5) measuring one or more properties of said polymer; (6) determining whether said one or measured polymer properties are within said feasible range: (7) validating said one or more measured polymer properties if said one or more measured polymer properties fall within the feasible range or invalidating said one or more measured polymer properties if said one or more measured polymer properties fall outside of the feasible range; (8) optionally updating said prediction model; (9) repeating said previous steps at least one or more times; and (10) thereby improving the prediction of polymer properties.

4 Claims, 3 Drawing Sheets

(56) References Cited

U.S. PATENT DOCUMENTS

| | | |
|---|---|---|
| 6,406,632 B1 | 6/2002 | Safir et al. |
| 6,687,621 B2 | 2/2004 | Schneiderman et al. |
| 2003/0065462 A1 | 4/2003 | Potyrailo |
| 2009/0177439 A1* | 7/2009 | Samples et al. ............... 702/179 |

OTHER PUBLICATIONS

Mcauley, K. B. et al., On-Line Inference of Polymer Properties in an Industrial Polyethylene Reactor, AIChE Journal, 1991, pp. 825-835, vol. 37, No. 6.

* cited by examiner

——— Operator Approved Resin Property Analysis
(Melt Flow in this example)
- - - - Resin Property Aim Value
——— Bed Average Resin Property Value
- - - - Instantaneous Resin Property Value
—··—··— High and Low Resin Property Specification Limits.
——— Unapproved Resin Property Analysis
············ High and Low Fault Detection Limits

METHOD FOR IMPROVING THE PREDICTION OF POLYMER PROPERTIES

CROSS-REFERENCE TO RELATED APPLICATIONS

This application is a non-provisional application claiming priority from the U.S. Provisional Patent Application No. 60/954,506, filed on Aug. 7, 2007, entitled "METHOD FOR IMPROVING THE PREDICTION OF POLYMER PROPERTIES AND A SYSTEM HAVING IMPROVED POLYMER PROPERTY PREDICTION CAPABILITIES," the teachings of which are incorporated by reference herein, as if reproduced in full hereinbelow.

FIELD OF INVENTION

The instant invention relates to a method for improving the prediction of polymer properties and a system having improved polymer property prediction capabilities.

BACKGROUND OF THE INVENTION

Polyolefin reactor systems typically rely on periodic or intermittent measurements of resin properties. The measurements are generally determined from a resin sample, which is extracted from the process system. Real-time measurements of polyolefin resin quality may be subject to substantial errors due to different reasons. These errors may be due to sampling issues, laboratory procedure misapplications, equipment malfunctions, or other causes. If the resin property measurements have substantial error, and then are subsequently used for reactor control, significant process disruption may be caused due to a response based on these improper measurements. However, if the sampled measurements can be marked as "likely erroneous," then it may be acted upon accordingly, and significantly better reactor control may be maintained. Currently, an operator decides if laboratory readings are appropriate for entry into the automation system, or for use in manual operation. This approach is often not effective due to the complexity in determining the feasibility of the reading. The complexity and uncertainty in the existing methodology results in operator decisions which are not sufficiently timely, consistent, or accurate. The improvement sought herein is to flag polymer property readings as acceptable or unacceptable before such measurements being used to manipulate reactor variables and conditions.

U.S. Pat. No. 5,260,882 describes a process for estimation of properties utilizing experimental information using constraints determined by chemical kinetics, statistical thermodynamics and molecular mechanics including experimental information on proposed polymeric or copolymeric substances of large molecules for the estimation of the physical properties of the substances by first defining the substances molecular chemical composition, second, estimating properties of the molecular chemical composition when 3-dimensionally folded, third, forming the composition into a polymeric cluster, fourth, estimating the physical properties of the polymeric cluster, and finally preparation of the polymeric substances having the properties as estimated.

U.S. Pat. No. 5,550,630 describes a method for analyzing the structures of chemical organic compounds, polymers, polynucleotides and peptides. The method uses the integrated intensity of spectral light absorption in wide or narrow regions of the ultraviolet and/or visible spectrum and relates these parameters additively to the structural characteristics of the analyzed chemical compound. For the analysis of polymers, nucleotides and/or peptides the integrated intensities of spectral absorption are used sequentially in narrow regions of the ultraviolet light which enables the determination of the molecular weight and the complete amino acid composition of the analyzed compound. All these procedures are interconnected in an automatic spectrophotometric structural analyzer.

U.S. Pat. No. 6,406,632 describes rapid characterization and screening of polymer samples to determine average molecular weight, molecular weight distribution and other properties is disclosed.

U.S. Pat. No. 6,687,621 describes a computational method for predicting a desired property and/or performance of polymers, and/or identifying and designing polymers that provide the desired property and/or performance, wherein the desired property can be provided by the neat, undiluted polymers, or diluted polymers in a composition. The method is a QSAR approach wherein the descriptors used are structural descriptors which are experimentally generated and/or derived from one or more analytical methods.

Despite the research efforts in developing polymer property prediction models, there is still a need for a method for improving the prediction of polymer properties and a system having improved polymer property prediction capabilities. Furthermore, there is a need for a method for automatically determining the feasibility of laboratory measurements using (1) the expected standard deviation of the sample polymer property measurements and/or (2) process models and estimates of measurement uncertainty.

SUMMARY OF THE INVENTION

The instant invention is a method for improving the prediction and subsequent control of polymer properties and a system having improved polymer property prediction capabilities. The method for improving the prediction of polymer properties according to instant invention comprises the following steps of: (1) providing a polymer; (2) providing a prediction model; (3) utilizing said prediction model to define an average polymer property prediction value; (4) determining a feasible range; (5) measuring one or more properties of said polymer; (6) determining whether said one or measured polymer properties are within said feasible range; (7) validating said one or more measured polymer properties if said one or more measured polymer properties fall within the feasible range or invalidating said one or more measured polymer properties if said one or more measured polymer properties fall outside of the feasible range; (8) updating said prediction model; (9) repeating said previous steps at least one or more times; and (10) thereby improving the prediction of polymer properties. The polymerization system having improved polymer property prediction capabilities according to instant invention comprises at least one polymerization reactor; an automated prediction model; means for measuring one or more polymer properties; means for detecting one or more erroneous measured polymer properties; and means for updating said automated predication model.

In one embodiment, the instant invention provides a method for improving the prediction of polymer properties comprising the following steps of: (1) providing a polymer; (2) providing a prediction model; (3) utilizing said prediction model to define an average polymer property prediction value; (4) determining a feasible range; (5) measuring one or more properties of said polymer; (6) determining whether said one or measured polymer properties are within said feasible range; (7) validating said one or more measured polymer properties if said one or more measured polymer properties fall within the feasible range or invalidating said one or more measured polymer properties if said one or more measured polymer properties fall outside of the feasible range; (8) updating said prediction model; (9) repeating said previous steps at least one or more times; and (10) thereby improving the prediction of polymer properties.

In an alternative embodiment, the instant invention provides a method for improving the prediction of polymer properties, in accordance with any of the preceding embodiments, except that the average polymer property prediction value is $x_p$.

In an alternative embodiment, the instant invention provides a method for improving the prediction of polymer properties, in accordance with any of the preceding embodiments, except that the feasible range is determined via $$x_{Low} = x_P\left(1 - \frac{\sigma}{x_p}\sqrt{-2\ln(1-f)}\right) - \frac{dx_p}{dt}T_u;$$

and $$x_{High} = x_P\left(1 + \frac{\sigma}{x_p}\sqrt{-2\ln(1-f)}\right) + \frac{dx_p}{dt}T_u;$$

wherein the polymer property prediction value is logarithmic; or the feasible range is determined via $$x_{Low} = x_P - \sigma\sqrt{-2\ln(1-f)} - \frac{dx_p}{dt}T_n;$$

and $$x_{High} = x_P + \sigma\sqrt{-2\ln(1-f)} + \frac{dx_p}{dt}T_u;$$

wherein the polymer property prediction value is non-logarithmic; and wherein $x_{Low}$ is the lowest value expected for the lab value;

$x_{High}$ is the highest value expected for the lab value;

f is the probability that the sample is part of the collection of samples;

$\sigma$ is the standard deviation of the lab measurement method;

$x_p$ is the model predicted bed average value;

$T_u$ is the amount of time uncertainty in the exact sample time; and $$\frac{dx_p}{dt}$$

is the derivative of $x_p$ with respect to time.

In an alternative embodiment, the instant invention provides a method for improving the prediction of polymer properties, in accordance with the preceding embodiment, except that the $$\frac{dx_p}{dt}$$

is determined via $$\frac{x_p^k - x_p^{k-1}}{t^k - t^{k-1}};$$

wherein k represents the current time; and k−1 represents the time one calculation interval previously.

In an alternative embodiment, the instant invention further provides a polymerization system having improved polymer property prediction capabilities comprising at least one polymerization reactor; an automated prediction model; means for measuring one or more polymer properties; means for detecting one or more erroneous measured polymer properties; and means for updating said automated predication model.

In an alternative embodiment, the instant invention further provides a method and a system for detecting erroneous polymer property measurement values before these values are used to manipulate reactor conditions.

In an alternative embodiment, the instant invention provides a polymerization system having improved polymer property prediction capabilities, in accordance with the preceding embodiment, except that the means for measuring one or more polymer properties is an automated device.

In an alternative embodiment, the instant invention provides a polymerization system having improved polymer property prediction capabilities, in accordance with any of the preceding embodiments, except that the means for detecting one or more erroneous measured polymer properties is an automated device.

In an alternative embodiment, the instant invention provides a polymerization system having improved polymer property prediction capabilities, in accordance with any of the preceding embodiments, except that the means for updating said automated predication model is an automated device.

In an alternative embodiment, the instant invention provides a polymerization system having improved polymer property prediction capabilities, in accordance with any of the preceding embodiments, except that the automated predication model is a computer model.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

DETAILED DESCRIPTION OF THE INVENTION

The instant invention is a method for improving the prediction of polymer properties and a system having improved polymer property prediction capabilities. The method for improving the prediction of polymer properties according to instant invention comprises the following steps of: (1) providing a polymer; (2) providing a prediction model; (3) utilizing said prediction model to define an average polymer property prediction value; (4) determining a feasible range; (5) measuring one or more properties of said polymer; (6) determining whether said one or measured polymer properties are within said feasible range; (7) validating said one or more measured polymer properties if said one or more measured polymer properties fall within the feasible range or invalidating said one or more measured polymer properties if said one or more measured polymer properties fall outside of the feasible range; (8) optionally updating said prediction model; (9) repeating said previous steps at least one or more times; and (10) thereby improving the prediction of polymer properties. The polymerization system having improved polymer property prediction capabilities according to instant invention comprises at least one polymerization reactor; an automated prediction model; means for measuring one or more polymer properties; means for detecting one or more erroneous measured polymer properties; and means for updating said automated predication model.

The term "polymer" is used herein to indicate a homopolymer, an interpolymer (or copolymer), or a terpolymer. The term "polymer," as used herein, includes interpolymers, such as, for example, those made by the copolymerization of ethylene or propylene with one or more alpha-olefin(s).

The term "interpolymer," as used herein, refers to polymers prepared by the polymerization of at least two different types of monomers. The generic term interpolymer thus includes copolymers, usually employed to refer to polymers prepared from two different types of monomers, and polymers prepared from more than two different types of monomers.

Any conventional homopolymerization or copolymerization reactions may be employed to produce the polymer compositions of the instant invention. Such conventional homopolymerization or copolymerization reactions include, but are not limited to, gas phase polymerization, slurry phase polymerization, liquid phase polymerization, and combinations thereof using conventional reactors, for example, gas phase reactors, loop reactors, stirred tank reactors, and batch reactors.

The polymer in the instant invention may be any polymer; for example, the polymer may be any polyolefin. The polyolefin may be any homopolymer and/or copolymer of one or more olefins. For example, the polyolefin may be a homopolymer of ethylene or a copolymer of ethylene with one or more α-olefins such as propylene, 1-butene, 1-pentene, 1-hexene, 1-heptene, 1-octene, 1-nonene, 1-decene, and 4-methyl-1-pentene. In the alternative, the polyolefin may be a homopolymer of propylene or a copolymer of propylene with one or more α-olefins such as ethylene, 1-butene, 1-pentene, 1-hexene, 1-heptene, 1-octene, 1-nonene, 1-decene, and 4-methyl-1-pentene.

Figure 1:
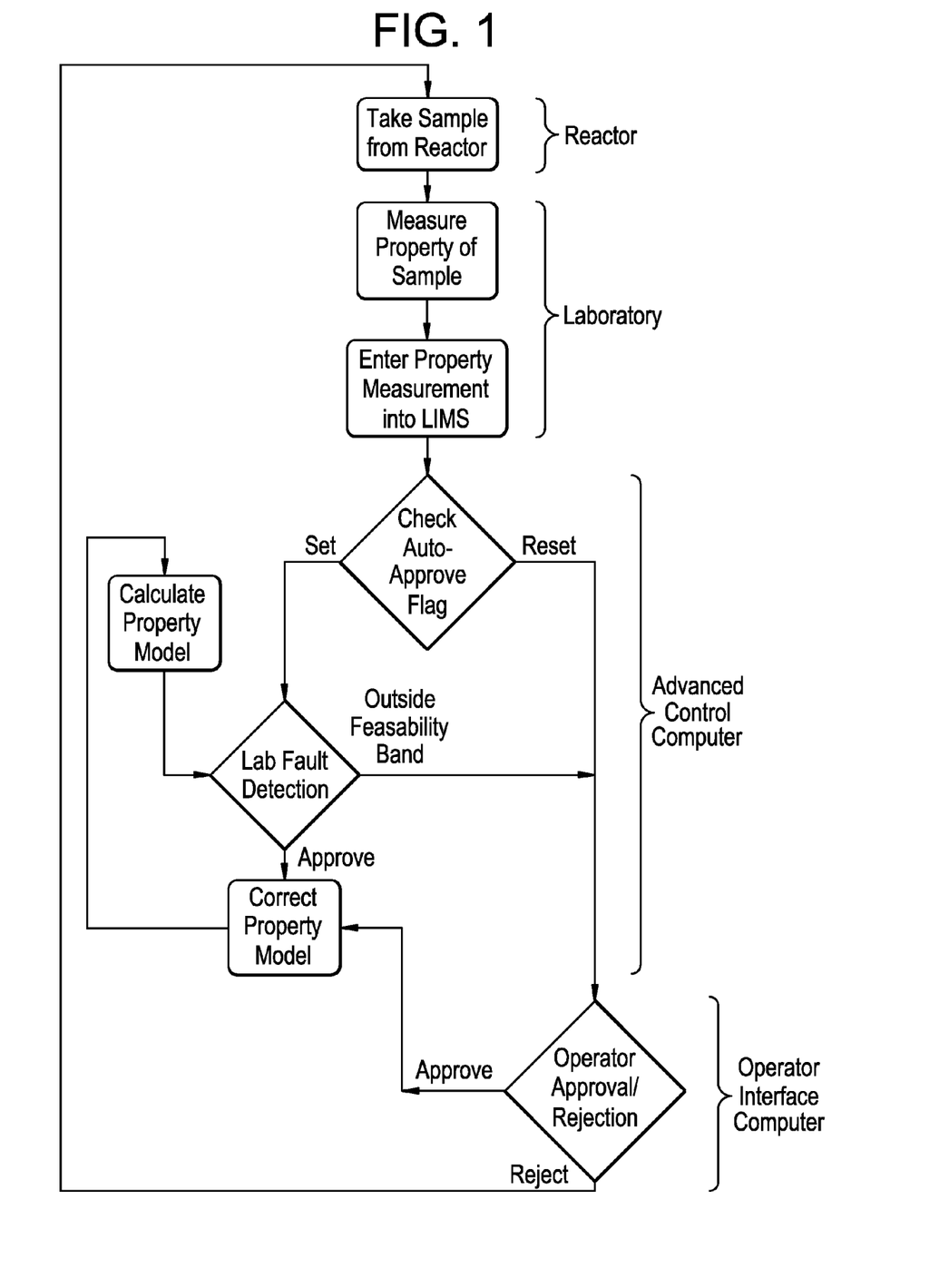
FIG. 1 is a flow chart illustrating how the instant invention operates.

Referring to FIG. 1, polymer samples are collected from a polymerization reactor. The polymer samples may be collected via any means capable of collecting such polymer samples. For example, the means for collecting polymer samples may be an automated device or a person.

The polymer samples are then analyzed to determine certain polymer properties. These polymer properties include, but are not limited to, density, melt index, melt flow rate, molecular weight, molecular weight distribution, weight and/or molar percentage of one or all atomic elements, average weight and/or molar percentage of each molecular group, number of each molecular group, number of each monomer, degree of unsaturation, degree of branching within a molecule and/or part of a molecule, weight percentage of each atomic element in a branching group, number of each molecular group in a branching group, number of each type and/or number of functional groups and/or their percentage of repeating units, monomer units or other subunits, viscosity, glass transition temperature, melting point, solubility, cloud point, heat capacity, interfacial tension, interfacial adhesion, refractive index, stress relaxation, sheer, conductivity, permeability, diamagnetic susceptibility, thermal conductivity, any other quantifiable polymer property, or combinations thereof. The polymer properties may be determined via any means capable of determining a numerical value for such properties; for example, the means for determining such polymer properties may include any analytical methods such as, but not limited to, nuclear magnetic resonance, infrared spectroscopy, UV/visible spectroscopy, fluorescence spectroscopy, quantitative hydrolysis, elemental analysis, chromatography, mass spectrometry, light scattering, osmometry, electrophoretic techniques, quantitative gravimetric analysis, and the like. Such analytical methods may be conducted via an automated device or a person.

Subsequently, these one or more measured polymer property values are entered into a laboratory information management system ("LIMS"), which may be any computer system. The one or more measured polymer property values may be entered into the LIMS via an automated device or a person. The computer application then checks to see if the one or more measured polymer properties is configured to be auto-approved or approved by the operator. The system may further provide recommendations to the operator regarding approval or rejection of one or more measured polymer properties. The operator may approve one or more measured polymer properties, or the operator may reject only those one or more measured properties falling outside of the acceptable range, that is, outlier values. The property model is calculated using the one or more measured polymer properties to estimate polymer properties in a cyclic recursive fashion.

Figure 2:
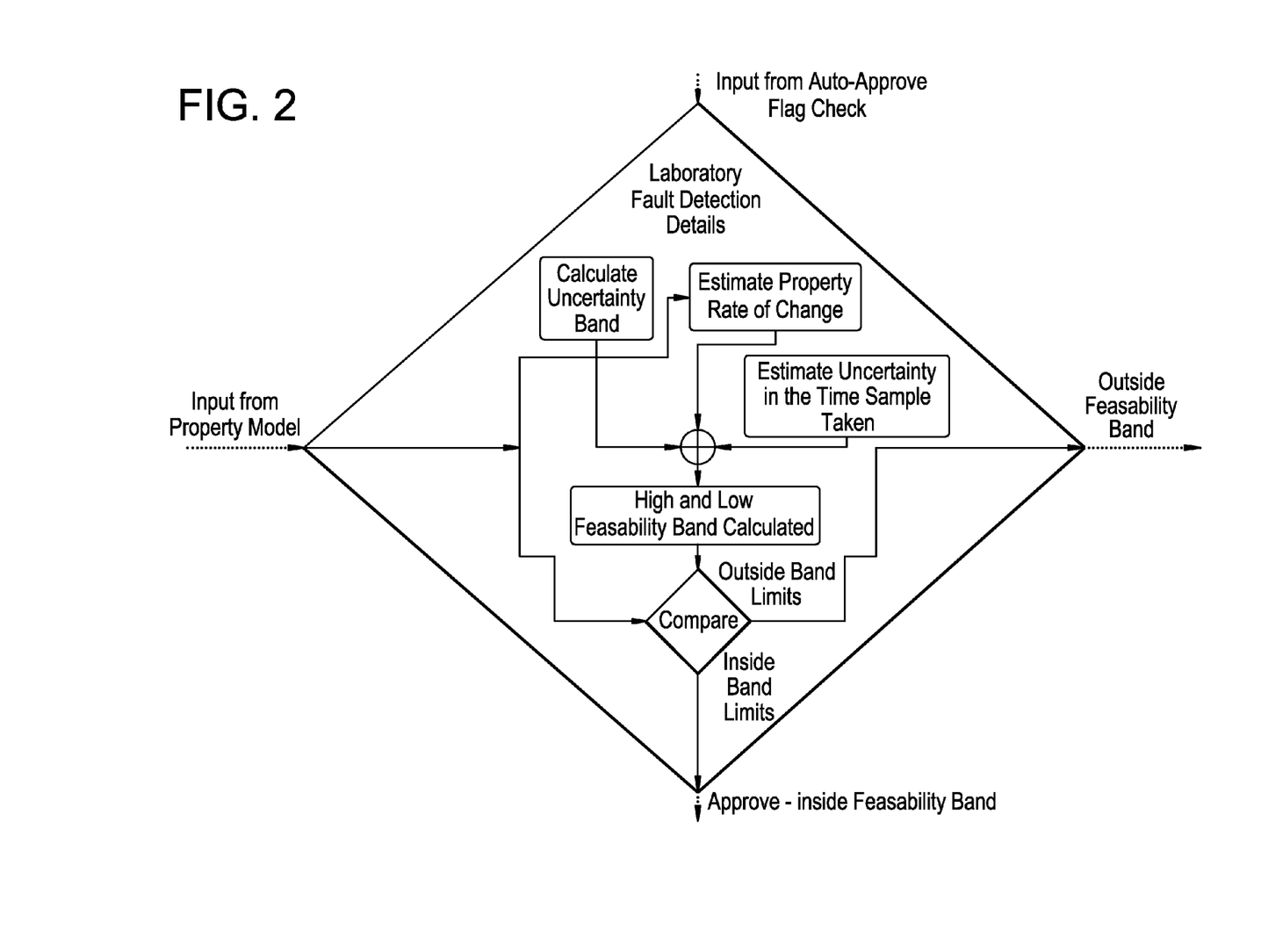
FIG. 2 is flow chart illustrating how one or more erroneous measured polymer properties are detected.

Referring to FIG. 2, the one or more polymer properties are then analyzed for outlier values, which are defined as those values residing outside of the feasibility range, as defined hereinbelow, according to the following steps. The laboratory fault detections may be achieved by performing calculations to determine if property values should be automatically approved or if the operator should make the approval decision. First, the uncertainty bands in one or more polymer property measurements are calculated via statistical methods or polymer property model input variations. The uncertainty bands in one or more polymer property measurements, for example, may be calculated by a sample standard deviation or using a polymer property model and input variation estimates. The uncertainty bands of the one or more measured polymer properties, as used herein, refer to lower limit and upper limit values defining the acceptable polymer property ranges. The standard deviation of the polymer property measurement may be determined off-line from historical or other pre-existing data, as well as online from recent history. The uncertainty estimates include model and input variable uncertainties, as well as uncertainty in the measured polymer property values and sample time. For example, a model may used to predict the laboratory measurement based on input variable measurements. This model is then augmented with the estimates of the input parameter uncertainties, and the uncertainty in the timing and value to the laboratory measurement.

The rate of change of one or more polymer property measurements are estimated via a polymer property model. The uncertainty of one or more polymer property measurements is estimated for the time that the one or more polymer property measurements are obtained. Feasibility bands for polymer property measurements are estimated, for example, using the augmented model. Feasibility bands for polymer property measurements, as used herein, refer to lower limit and upper limit values defining the physically possible polymer properties based on the prediction model. The feasibility range is further described hereinbelow. Preferably, the lower limit and upper limit values of the feasibility bands define a narrow range. The actual measured polymer properties are compared to those high and low feasibility bands or limits at the time the samples were taken from the reactor. The measured polymer properties are validated or invalidated based on the comparison of the measured polymer properties to the high and low feasibility limits. The validated and invalidated measured polymer property samples are marked as such, and they are being used for controlling reactor conditions; thus, flagging unreliable polymer property measurements before these measurements are acted upon, and facilitating appropriate reactor control decision makings. The laboratory fault detection steps mentioned above may be repeated as necessary. The comparison of the one or more polymer properties with the high and low feasibility limits may be conducted via an automated device such as a computer or a person.

The feasibility range may be determined via $$x_{Low} = x_P\left(1 - \frac{\sigma}{x_p}\sqrt{-2\ln(1-f)}\right) - \frac{dx_p}{dt}T_u;$$

and $$x_{High} = x_P\left(1 + \frac{\sigma}{x_p}\sqrt{-2\ln(1-f)}\right) + \frac{dx_p}{dt}T_u;$$

wherein the polymer property prediction value is logarithmic; or in the alternative, the feasible range is preferably determined via $$x_{Low} = x_P - \sigma\sqrt{-2\ln(1-f)} - \frac{dx_p}{dt}T_u;$$

and $$x_{High} = x_P + \sigma\sqrt{-2\ln(1-f)} + \frac{dx_p}{dt}T_u;$$

wherein the polymer property prediction value is non-logarithmic; and wherein
  $x_{Low}$ is the lowest value expected for the lab value;
  $x_{High}$ is the highest value expected for the lab value;
  f is the probability that the sample is part of the collection of samples;
  $\sigma$ is the standard deviation of the lab measurement method;
  $x_p$ is the model predicted bed average value;
  $T_u$ is the amount of time uncertainty in the exact sample time; and $$\frac{dx_p}{dt}$$

is the derivative of $x_p$ with respect to time.
The $$\frac{dx_p}{dt}$$

is preferably determined via $$\frac{x_p^k - x_p^{k-1}}{t^k - t^{k-1}};$$

wherein
  k represents the current time; and
  k−1 represents the time one calculation interval previously.
In the alternative, the feasibility range may be determined via $x_{Low} = x_p(1-\text{delta})_u$; and $x_{High} = x_p(1+\text{delta})$, and wherein $x_p$ is the model predicted bed average value.

EXAMPLES

The following examples illustrate the present invention but are not intended to limit the scope of the invention. The examples of the instant invention demonstrate that unreliable polymer property measurements are flagged before these measurements are acted upon; thus making appropriate reactor control decision makings. Furthermore, these examples show that the instant invention provides the means for detecting erroneous polymer property measurement values before these values are used to manipulate reactor conditions.

Example 1

Figure 3:
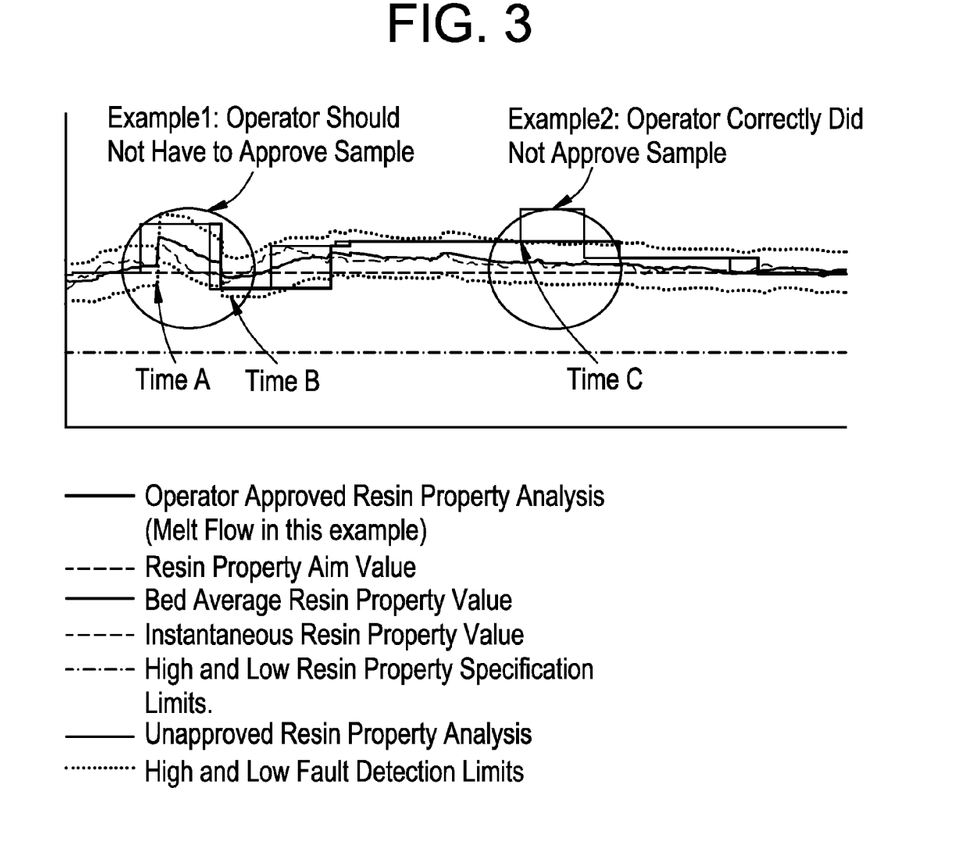
FIG. 3 is a graphical illustration of automated detection of one or more erroneous measured polymer properties to improve the prediction of such polymer properties.

Example 1 is a comparative example, showing unreliable polymer property measurements may cause the wrong action to be taken. In a gas phase polymerization of polypropylene, the instant invention was utilized to flag unreliable polymer property measurements. The data recorded, as shown in FIG. 3, shows that the operator ignored the warning from the laboratory fault detection system; thus, approving the sample at "Time A." This caused the hydrogen to propylene molar ratio setpoint to be inappropriately lowered by the polymer property controller in response to a "bad" reading. The result of this incorrect decision may be seen in the next laboratory sample, shown at "Time B", where the Melt Flow laboratory reading was apparently low.

Example 2

Example 2 is an inventive example, showing that unreliable polymer property measurements are flagged before these measurements are acted upon; thus making appropriate reactor control decision makings. In a gas phase polymerization of polypropylene, the instant invention was utilized to flag unreliable polymer property measurements. The data recorded, as shown in FIG. 3, shows that the operator made the correct decision not approve the lab sample at "Time C" in agreement with the recommendation of the laboratory fault detection system; thus, avoiding a process disruption.

The present invention may be embodied in other forms without departing from the spirit and the essential attributes thereof, and, accordingly, reference should be made to the appended claims, rather than to the foregoing specification, as indicating the scope of the invention.

We claim:
1. A method for improving the prediction of polymer properties comprising the steps of:
  providing a polymer;
  providing a prediction model based on material balance and polymer properties;

utilizing said prediction model to define an average polymer property prediction value, wherein said average polymer property prediction value is $x_p$;
determining a feasible range;
measuring one or more properties of said polymer;
determining whether said one or more measured polymer properties are within said feasible range;
validating said one or more measured polymer properties if said one or more measured polymer properties fall within the feasible range or invalidating said one or more measured polymer properties if said one or more measured polymer properties fall outside of the feasible range;
updating said prediction model;
repeating said previous steps at least one or more times until updating said prediction model at least one more time; and
thereby improving the prediction of polymer properties;
wherein said feasible range is determined via $$x_{Low} = x_P\left(1 - \frac{\sigma}{x_p}\sqrt{-2\ln(1-f)}\right) - \frac{ax_p}{dt}T_u;$$

and $$x_{High} = x_P\left(1 + \frac{\sigma}{x_p}\sqrt{-2\ln(1-f)}\right) + \frac{dx_p}{dt}T_u;$$

wherein said polymer property prediction value is logarithmic, and wherein
$x_{Low}$ is the lowest value expected for the lab value;
$x_{High}$ is the highest value expected for the lab value;
f is the probability that the sample is part of the collection of samples;
σ is the standard deviation of the lab measurement method;
$x_p$ is the model predicted bed average value;
$T_u$ is the amount of time uncertainty in the exact sample time; and $$\frac{dx_p}{dt}$$

is the derivate of $x_p$ with respect to time.

2. The method for improving the prediction of polymer properties according to claim 1, wherein said $$\frac{dx_p}{dt}$$

is determined via $$\frac{x_p^k - x_p^{k-1}}{t^k - t^{k-1}};$$

wherein
k represents the current time; and
k−1 represents the time one calculation interval previously.

3. A method for improving the prediction of polymer properties comprising the steps of:
providing a polymer;
providing a prediction model based on material balance and polymer properties;
utilizing said prediction model to define an average polymer property prediction value, wherein said average polymer property prediction value is $x_p$;
determining a feasible range;
measuring one or more properties of said polymer;
determining whether said one or more measured polymer properties are within said feasible range;
validating said one or more measured polymer properties if said one or more measured polymer properties fall within the feasible range or invalidating said one or more measured polymer properties if said one or more measured polymer properties fall outside of the feasible range;
updating said prediction model;
repeating said previous steps at least one or more times until updating said prediction model at least one more time; and
thereby improving the prediction of polymer properties;
wherein said feasible range is determined via $$x_{Low} = x_P - \sigma\sqrt{-2\ln(1-f)} - \frac{dx_p}{dt}T_n;$$

and $$x_{High} = x_P + \sigma\sqrt{-2\ln(1-f)} + \frac{dx_p}{dt}T_u;$$

wherein said polymer property prediction value is non-logarithmic, and wherein
$x_{Low}$ is the lowest value expected for the lab value;
$x_{High}$ is the highest value expected for the lab value;
f is the probability that the sample is part of the collection of samples;
σ is the standard deviation of the lab measurement method;
$x_p$ is the model predicted bed average value;
$T_u$ is the amount of time uncertainty in the exact sample time; and $$\frac{dx_p}{dt}$$

is the derivative of $x_p$ with respect to time.

4. A method for improving the prediction of polymer properties comprising the steps of:
providing a polymer;
providing a prediction model based on material balance and polymer properties;
utilizing said prediction model to define an average polymer property prediction value, wherein said average polymer property prediction value is $x_p$;
determining a feasible range;
measuring one or more properties of said polymer;
determining whether said one or more measured polymer properties are within said feasible range;
validating said one or more measured polymer properties if said one or more measured polymer properties fall within the feasible range or invalidating said one or more measured polymer properties if said one or more measured polymer properties fall outside of the feasible range;
updating said prediction model;
repeating said previous steps at least one or more times until updating said prediction model at least one more time; and thereby improving the prediction of polymer properties; wherein said feasible range is determined via $x_{Low}=x_p(1-delta)_u$; and
$x_{High}=x_p(1+delta)$; wherein $x_p$ is the model predicted bed average value.

* * * * *